United States Patent [19]

Cioca

[11] Patent Number: 4,591,501
[45] Date of Patent: May 27, 1986

[54] COSMETIC AND PHARMACEUTICAL SHEET MATERIAL CONTAINING POLYPEPTIDES

[75] Inventor: Gheorghe Cioca, Coatesville, Pa.

[73] Assignee: Seton Company, Newark, N.J.

[21] Appl. No.: 610,617

[22] Filed: May 16, 1984

Related U.S. Application Data

[60] Continuation of Ser. No. 459,209, Jan. 19, 1983, which is a division of Ser. No. 253,739, Apr. 13, 1981, abandoned.

[51] Int. Cl.$^4$ .......... A61K 9/70; A61F 13/00; A61L 15/03
[52] U.S. Cl. .......... 424/28; 106/124; 106/161; 128/76 B; 424/36; 424/78; 514/773; 514/774; 514/801; 514/844; 514/947; 514/953; 604/303; 604/304; 604/290
[58] Field of Search .......... 106/124, 161; 128/76 B, 128/268; 424/283, 678, 359; 514/773, 774, 801, 844, 947, 953

[56] References Cited

U.S. PATENT DOCUMENTS

| | | | |
|---|---|---|---|
| 922,428 | 5/1909 | Hannig | 128/76 B |
| 1,955,075 | 4/1934 | Lienig | 106/124 |
| 2,001,862 | 5/1935 | Battey | 128/76 B |
| 2,002,449 | 5/1935 | Dohm | 128/76 B |
| 2,017,596 | 10/1935 | Hoffman | 424/28 |
| 2,385,802 | 10/1945 | Ferry | 106/124 |
| 2,385,803 | 10/1945 | Cohn et al. | 106/124 |
| 2,413,007 | 12/1946 | Srere | 106/161 |
| 2,434,906 | 1/1948 | Carlton et al. | 106/161 |
| 2,540,247 | 2/1951 | Dillon | 128/76 B |
| 2,657,972 | 11/1953 | Woodward | 260/78 A |
| 2,693,438 | 11/1954 | Ward | 424/28 |
| 2,726,982 | 12/1955 | Ochs et al. | 424/359 |
| 2,728,339 | 12/1955 | Elmhirst | 128/76 B |
| 2,882,892 | 4/1959 | Kosior | 128/76 B |
| 2,923,291 | 2/1960 | Lagoma | 128/76 B |
| 3,214,338 | 10/1965 | Ehrlich | 424/28 |
| 3,370,969 | 2/1968 | Powell et al. | 106/124 |
| 3,483,289 | 12/1969 | Michaelson et al. | 106/161 X |
| 3,523,807 | 8/1970 | Gerendas | 106/124 |
| 3,615,715 | 10/1971 | Mullen | 106/124 |
| 3,649,347 | 3/1972 | Battista | 106/161 |
| 3,803,300 | 4/1974 | Pospischil | 424/28 |
| 3,839,590 | 10/1974 | Battista | 424/359 |
| 3,867,520 | 2/1975 | Mori et al. | 424/36 |
| 3,907,580 | 9/1975 | Van Ham | 106/158 |
| 3,949,741 | 4/1976 | Hofmann | 128/76 B |
| 3,991,184 | 11/1976 | Kludas et al. | 424/359 |
| 4,117,837 | 10/1978 | Remiro | 128/76 B |
| 4,131,650 | 12/1978 | Braumer et al. | 424/28 |
| 4,179,333 | 12/1979 | Braeumer et al. | 424/359 |
| 4,210,633 | 7/1980 | Takruri et al. | 424/28 |
| 4,215,693 | 8/1980 | Rothman et al. | 106/124 |

FOREIGN PATENT DOCUMENTS

| | | | |
|---|---|---|---|
| 2804024 | 8/1979 | Fed. Rep. of Germany | 424/359 |
| 1505318 | 12/1967 | France . | |
| 2245161 | 3/1975 | France . | |
| 7392522 | 11/1973 | Japan . | |
| 7430525 | 3/1974 | Japan . | |
| 7445952 | 5/1974 | Japan . | |
| 7448728 | 12/1974 | Japan . | |
| 76112511 | 10/1976 | Japan . | |
| 7738016 | 3/1977 | Japan . | |
| 7850320 | 5/1978 | Japan . | |
| 54-154683 | 5/1979 | Japan | 424/359 |
| 56-4780 | 1/1981 | Japan . | |
| 933668 | 8/1963 | United Kingdom | 424/78 |
| 910004 | 11/1972 | United Kingdom | 424/359 |
| 1298223 | 11/1972 | United Kingdom | 424/359 |
| 219116 | 3/1973 | U.S.S.R. . | |

OTHER PUBLICATIONS

Plastics Engineering Handbook, Society of the Plastics Industry, Inc., Reinhold Publishing Corporation, New York, 1954, p. 332.

Ban et al. Pharmazie 29(9); 597–602 (1974) Herstellung Von Filmbildenden Praparaten Mit Wirkvng Gegen Akne.

Spira et al. J. Biomed. Mater. Res. 3:213–234 (1969) Evaluation of Synthetic Fabrics as Artificial Skin Grafts to Experimental Burn Wounds.

*Primary Examiner*—Shep K. Rose
*Attorney, Agent, or Firm*—Webb, Burden, Robinson & Webb

[57] ABSTRACT

A flexible continuous film is comprised of a physical admixture of a polypeptide, a plasticizer and a film-forming flexible polymer. When the film is moistened, the polypeptides exude therefrom.

6 Claims, 2 Drawing Figures

COSMETIC AND PHARMACEUTICAL SHEET MATERIAL CONTAINING POLYPEPTIDES

This application is a continuation of application Ser. No. 459,209, filed Jan. 19, 1983, which is a division of application Ser. No. 253,739, filed Apr. 13, 1981 now abandoned.

BACKGROUND OF THE INVENTION

This invention relates to flexible continuous films containing polypeptides. Polypeptides including polyamino acids have been found to be useful in the cosmetic and pharmaceutical fields. It is accepted in the formulation of cosmetics, that polypeptides provide a beneficial effect to creams and topically applied preparations. Typically, the polypeptides are formulated into such creams and topical preparations and the preparation is applied in a fluid form and allowed to contact the skin of the user for a predetermined time. Among the polypeptides that have been useful are the polyamino acids derived from protein and the proteins themselves. Two particularly useful proteins which have been incorporated into cosmetics are collagen and elastin along with derivatives thereof. Collagen has been found to have advantageous effects when topically applied along with the polyamino acids derived therefrom. Likewise, elastin has been proposed and used in such cosmetic preparations.

In another aspect, it has been found that collagen, when formulated with antiseptics and other similar materials, is useful in promoting healing of skin and more particularly in the promotion of healing in burn victims. Such pharmaceutical preparations require a sterile environment for the production of the preparation from the time it is manufactured to the time that it is applied to the burn victim. Thus, extreme care must be taken in the manufacture and transport to insure a sterile product.

It has long been desirable to provide an easily dispensed polypeptide containing preparation in a controlled dosage through a conveniently applied material. However, because of the high molecular weight of polypeptides and their specific chemical structure, it has been difficult to form films thereof because they tend to be brittle and difficult to apply. Further, any film containing polypeptides for topical application must be extremely flexible to fit the contour of the particular part of the body to be treated.

In accordance with the present invention, polypeptides are provided in the form of a continuous film which is tough and flexible and which provides transfer of the polypeptides onto the skin of the person to be treated.

BRIEF DESCRIPTION OF THE INVENTION

A flexible continuous film is comprised of an admixture of a polypeptide, a plasticizer and a film-forming flexible polymer. The film, when moistened, will exude the polypeptide.

"Polypeptide" as used herein, means and refers to polyamino acids derived from protein along with the proteins themselves. The polyamino acids useful in the practice of the invention are those polyamino acids having a molecular weight of at least 3,000. Preferably, the polyamino acids are derived from collagen.

collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a fibril and the fibrils align with an axial periodicity of about 640 Å.

In young animals there is little intermolecular and interfibular crosslinking which provides for some degree of solubility of the collagen. However, during the aging process both intermolecular and interfibular crosslinking occurs thus making the collagen insoluble. In order to process insoluble collagen to form polyamino acids, the long chains must be broken along with the interfibular and intrafibular bonds. These polyamino acids derived from collagen are formed by enzymatically digesting the protein to form short chain oligopeptides, i.e. polyamino acids. Another method of forming polyamino acids from collagen is by the process disclosed in U.S. patent application Ser. No. 113,694 of Gheorghe Cioca et al., filed Jan. 21, 1980 entitled "Oligopeptides Derived From Collagen", incorporated herein by reference. In this method of producing polyamino acids, collagen is hydrolyzed to form oligopeptides in a molecular weight range of about 5,000 to 20,000. This preferred method produces polyamino acids which are substantially pure and are useful in the practice of the invention in both cosmetic and pharmaceutical applications. In addition to the polyamino acids, soluble collagen, per se, can be incorporated into the continuous film of the invention. Thus, the collagen which is present in younger animals is suitable for incorporation into the film whereas when the collagen is from older animals, it must be processed to form a soluble product. One such method of forming soluble collagen is disclosed in U.S. patent application Ser. No. 074,738 filed Sept. 12, 1979 of Gheorghe Cioca entitled "Process for Preparing Macromolecular Biologically Active Collagen", incorporated herein by reference. In accordance with the process disclosed in that application, soluble collagen is prepared which can be readily incorporated into the continuous film in accordance with the invention.

Preferably, the polyamino acids are incorporated into the film at a level of 25 to 75 percent by weight and more preferably 40 to 60 percent by weight. When soluble collagen is incorporated into the film, it is present at a level of 3 to 5 percent by weight.

The plasticizers useful in the practice of the invention are those which are water soluble and preferably topically nonirritating and possessing relatively high boiling points, i.e. above 150° C. Typical plasticizers useful in the practice of the invention are glycerol, dipropylene glycol, diethylene glycol and the like. Preferably, the plasticizers are present at a level of 20 to 40 percent by weight and more preferably 30 to 40 percent by weight. The plasticizer is necessary so that the continuous film is flexible during fabrication and transportation, and maintains its flexibility in use. Other plasticizers known to those skilled in the art can also be used so long as they impart the requisiste flexibility of the film and are water soluble and nonvolatile.

The film-forming polymer useful in the practice of the invention is one which is also water soluble and is capable of forming a homogeneous solution with the polypeptide and the plasticizer in water. A most preferred polymer is polyvinyl alcohol. Polyvinyl alcohol is preferred because of its solubility in hot water and insolubility in cold water. Thus, the polyvinyl alcohol can be dissolved in water along with the plasticizer and polypeptide and the solution heated to form a flowable admixture. After film-forming and subsequent evaporation of water and other solvents which may be present in the admixture, the polymer forms a tough flexible film along with the polypeptide and the plasticizer. When contacted with cold water, the polyvinyl alcohol does not dissolve but the polypeptide is mobilized and exudes fom the film onto the skin of the person being treated. In addition, although polyvinyl alcohol is water soluble, it does not have sufficient acidity or basicity to adversely react with skin. Preferably, the film-forming polymer is present at a level of 10 to 20 percent by weight.

In a typical formulation and procedure for preparing the flexible continuous film in accordance with the invention, a 5 to 15 percent by weight film-forming polymer solution is made in water. In addition to water other solvents such as methanol, ethanol, butyanol or the like may be added. The polymer solution is admixed with a solution of polypeptide and in the case of polyamino acids, a 30 percent solution of the polyamino acids in water and, if desired, a lower alcohol having up to 4 carbon atoms. The plasticizer is then added and the components form a homogeneous solution or dispersion. The solution or dispersion can then be coated by conventional techniques and the water and other solvent (alcohol in this case) evaporated to form the flexible continuous film. Exemplary of such methods is to coat the solution or dispersion onto a release paper by way of a print roll. The film so coated can be wet laminated onto a nonwoven or woven porous material and the composite dried free of solvent and water. After drying, the composite can be overcoated with a solution and dried to form a film of the desired thickness.

The nonwoven or woven material provides integrity to the final film supplying additional strength and tenacity for shipment and use. The nonwoven material may be in the form of a netting or thin batt of natural or synthetic fiber and most preferably a synthetic fiber of nylon or the like. The woven or nonwoven material has a preferably thickness of 2.9 to 4.9 mils and an approximate density of 48 grams/sq. yd.

Other methods known to those skilled in the coating art may be utilized to form the flexible film of the invention.

The following Examples will more fully illustrate the invention.

EXAMPLE I

To a suitable container was charged: 100 parts by weight of an 8 percent polyvinyl alcohol solution in 70/30, water/ethanol; 100 parts by weight of a 30 percent solution of polyamino acids acids drom collagen having a molecular weight range of 2,000 to 5,000 in 70/30, water/ethanol; and 25 grams of glycerol. The ingredients were homogeneously mixed at room temperature to form a physical admixture of components.

The above solution was coated via a print roll onto Daubert's 1-55 SCK-1 transfer paper to a thickness of 5 wet mils. The coated paper was wet laminated with nonwoven polyester material Kendall No. 9605 having the following specifications. The above composite was dried for 3 to 5 minutes at 185° F. The composite was overcoated with the same solution with a print roll applying 12 wet mils of solution thereto. The sample was again dried for 5 to 10 minutes at 185° F. The material was again overcoated with the same solution with about 10 mils wet thickness. The sample was dried for 10 minutes at 185° F. and 3 to 5 minutes at 300° F. After drying, the material was allowed to cool to room temperature and was cut into sheets and packaged.

In one particular use for the invention, holes were cut like a mask so that the material could be used as a cosmetic face mask. In using the material as a face mask, the material is wet with cold water and applied to the face. The moisture causes the polypeptides to exude from the film and transfer along with the glycerol to the face. The polyvinyl alcohol remains as a continuous film and after 10 minutes to 1 hour of being applied to the face, the mask is removed.

EXAMPLE II

Example I was repeated except that 3.5 parts by weight based on the weight of sheet material of macromolecular biologically active collagen produced in accordance with Example I of U.S. patent application Ser. No. 074,738, filed Sept. 12, 1979 of Gheorghe Cioca entitled "Process for Preparing Macromolecular Biologically Active Collagen" was added as a 2.75 percent solution in dipropylene glycol. The flexible continuous film prepared in accordance with Example II can also be used as a cosmetic face mask.

EXAMPLES III, IV & V

Example II was repeated except 0.00001 percent of merthiolate for Example III, iodine for Example IV, and silver sulfodiazine for Example V were incorporated into the solution prior to coating. The flexible continuous films are cut into appropriate sizes and moistened and used for burn dressings. The collagen, which is recognized as advantageous in the treatment of burns, is released over a period of time up to about 30 days, thus promoting healing of skin burns.

EXAMPLE VI

Example I was repeated except that 3.5 parts by weight of elastin is added to the solution. The product in accordance with Example VI is useful as a cosmetic face mask.

Thus, in accordance with the present invention, a flexible continuous film containing polypeptides is provided wherein when the film is moistened, the polypeptides exude therefrom. The film of the invention is useful in treating burns and other pharmaceutical and cosmetic applications.

DETAILED DESCRIPTION OF THE DRAWINGS

Figure 1:
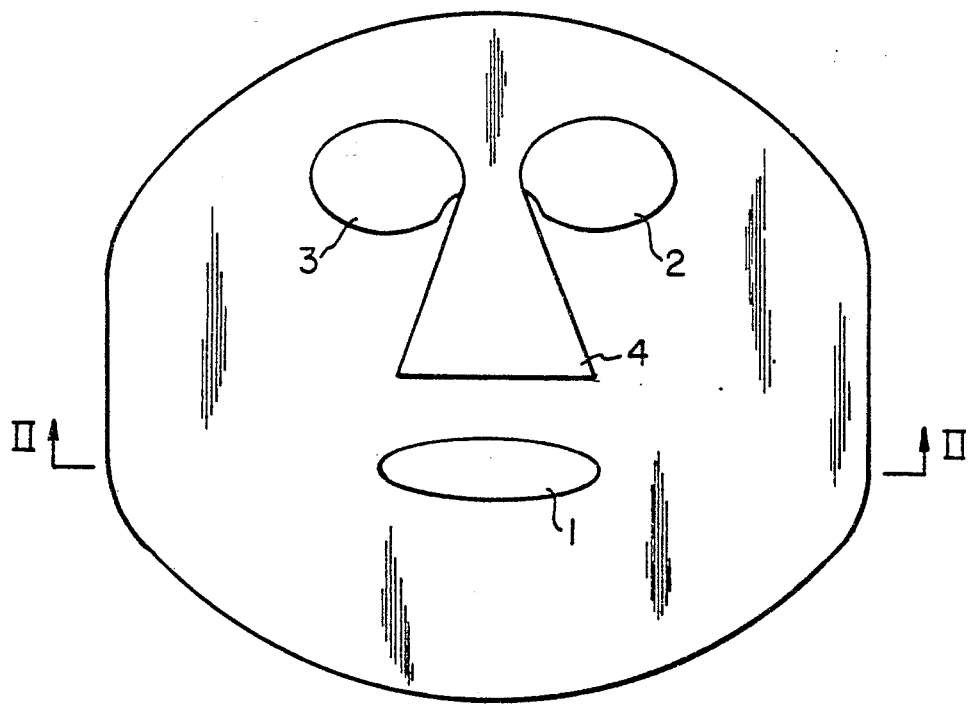
FIG. 1 is a face mask in accordance with the invention.
Figure 2:
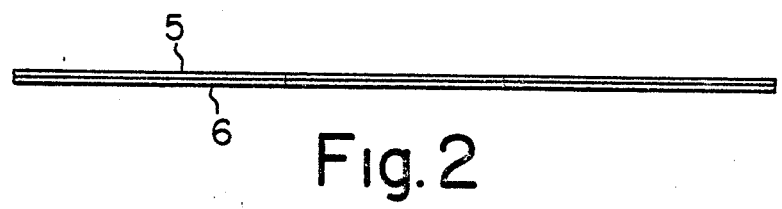
FIG. 2 is a cross section of the face mask shown in FIG. 1 taken along the 2—2 line.

A face mask shown in FIGS. 1 and 2 is comprised of the flexible continuous film 5 mounted on the release sheet 6. The mask is provided with holes for the eyes 2 and 3 and is fitted with slits so as to form a flap 4 for use over the nose of the user. A hole 1 is provided so that the wearer can breathe.

In use, the material is wet with water and applied to the face. The moisture causes the polypeptides in the film 5 to exude from the film and transfer, along with the glycerol or other plasticizer, to the face. The transfer release sheet is removed after immediately applying the material to the face.

Thus, although the invention has been described with reference to particular materials and particular procedures, it is only to be limited so far as is set forth in the accompanying claims.

I claim:

1. In the method of cosmetically treating human skin by applying polypeptides topically thereto, the improvement comprising:
   (a) contacting the skin with a water-moistened sheet material in the form of a cosmetic face mask, consisting essentially of water-moistened polypeptides formed of a flexible continuous film which, moistened, exudes said polypeptide while remaining as a continuous film, comprising a homogeneous physical admixture of:
   (i) a polypeptide selected from the group consisting of collagen, elastin and polypeptides derived from collagen and elastin and having a molecular weight of at least 2,000 to 20,000, wherein when said polypeptide is derived from collagen and elastin it is present at a level of 25 to 75 percent by weight based on the weight of the admixture and when said polypeptide is collagen or elastin it is present at a level of 3 to 5 percent by weight based on the weight of said admixture;
   (ii) 20 to 40 percent by weight of glycerol, dipropylene glycol, diethylene glycol, or mixtures thereof, as a water soluble non-volatile plasticizer having a boiling point in excess of about 150° C.; and
   (iii) 10 to 20 percent by weight of a film-forming polyvinyl alcohol which is soluble in hot water and insoluble in cold water;
   for a time sufficient to allow said polypeptides to exude from said sheet material onto said skin; and
   (b) removing said sheet material from said treated skin.

2. The improvement of claim 1 wherein said polypeptides are selected from the group consisting of collagen and polypeptides derived from collagen.

3. The improvement of claim 1 wherein said polypeptides are present at a level of 40 to 60 percent by weight.

4. The improvement of claim 1 wherein the polypeptides are selected from the group consisting of elastin and polypeptides derived from elastin.

5. The improvement of claim 1 wherein the sheet material is in the form of a cosmetic face mask provided with holes and slits and mounted on a release sheet.

6. The improvement of claim 1 wherein said sheet material is saturated with cold water prior to contact with the skin.

* * * * *